US011517604B2

United States Patent
Ko et al.

(10) Patent No.: US 11,517,604 B2
(45) Date of Patent: Dec. 6, 2022

(54) **METHOD FOR PREPARING *PLECTRANTHUS AMBOINICUS* FRACTION HAVING ANTI-ARTHRITIS ACTIVITY**

(71) Applicant: ONENESS BIOTECH CO., Taipei (TW)

(72) Inventors: Feng-Nien Ko, Taipei (TW); Jen-Wei Chen, Taipei (TW); Wen-Ling Yang, Taipei (TW)

(73) Assignee: ONENESS BIOTECH CO., Taipei (TW)

( * ) Notice: Subject to any disclaimer, the term of this patent is extended or adjusted under 35 U.S.C. 154(b) by 0 days.

(21) Appl. No.: 15/496,521

(22) Filed: Apr. 25, 2017

(65) Prior Publication Data

US 2017/0354701 A1 Dec. 14, 2017

Related U.S. Application Data

(60) Continuation of application No. 14/328,475, filed on Jul. 10, 2014, now abandoned, which is a division of application No. 13/680,689, filed on Nov. 19, 2012, now abandoned.

(30) Foreign Application Priority Data

Nov. 22, 2011 (TW) .................................. 100142840

(51) Int. Cl.
*A61K 36/53* (2006.01)
*A61K 31/05* (2006.01)
*A61K 31/353* (2006.01)

(52) U.S. Cl.
CPC .............. *A61K 36/53* (2013.01); *A61K 31/05* (2013.01); *A61K 31/353* (2013.01); *A61K 2236/30* (2013.01)

(58) Field of Classification Search
CPC ....... A61K 36/53; A61K 31/05; A61K 31/353
See application file for complete search history.

(56) References Cited

U.S. PATENT DOCUMENTS

| | | | | |
|---|---|---|---|---|
| 7,531,194 | B2 * | 5/2009 | Wu | ........................ A61K 36/53 424/725 |
| 2007/0237841 | A1 * | 10/2007 | Wu | ....................... A61K 9/0014 424/725 |
| 2008/0069911 | A1 | 3/2008 | Wu et al. | |
| 2009/0060985 | A1 * | 3/2009 | Wu | ........................ A61K 36/23 424/445 |
| 2009/0076143 | A1 | 3/2009 | Wong et al. | |

FOREIGN PATENT DOCUMENTS

| | | | |
|---|---|---|---|
| EP | 1 925 310 | A1 | 5/2008 |
| EP | 2 025 340 | A1 | 2/2009 |
| WO | WO 2009/106125 | A1 | 9/2009 |

OTHER PUBLICATIONS

Patel, et al., "Diuretic activity of leaves of Plectranthus amboinicus (Lour) Spreng in male albino rats," Pharmacognosy Res., Mar.-Apr. 2010, vol. 2, No. 2, pp. 86-88.
Perry, et al, "Salvia for dementia therapy: review of pharmacological activity and pilot tolerability clinical trial," Pharmacology, Biochemistry and Behavior, 2003, vol. 75, pp. 651-659.

* cited by examiner

*Primary Examiner* — Jared Barsky
(74) *Attorney, Agent, or Firm* — Birch, Stewart, Kolasch & Birch, LLP (57) ABSTRACT

The invention provides an extract of *Plectranthus amboinicus* (Lour.) Spreng enriching anti-arthritis activity, which is obtained by eluting the crude extract of *Plectranthus amboinicus* (Lour.) Spreng using 50%~95% alcoholic solution or solvents such as hexane and/or ethyl acetate. Also provided is a method for treating arthritis comprising such extract.

2 Claims, 8 Drawing Sheets

METHOD FOR PREPARING *PLECTRANTHUS AMBOINICUS* FRACTION HAVING ANTI-ARTHRITIS ACTIVITY

This application is a Continuation of U.S. patent application Ser. No. 14/328,475 filed on Jul. 10, 2014, which is a Division of U.S. patent application Ser. No. 13/680,689 filed on Nov. 19, 2012, which claims priority under 35 U.S.C. § 119(a) to Patent Application No. 100142840 filed in Taiwan on Nov. 22, 2011, all of which are hereby expressly incorporated by reference into the present application.

FIELD OF THE INVENTION

The present invention relates to a plant extract, which in particular, is a fraction of *Plectranthus amboinicus* (Lour.) Spreng enriching anti-arthritis activities.

BACKGROUND OF THE INVENTION

Arthritis is the most common autoimmune disease. The hallmarks of the disease are inflammation of the synovial tissues with progressive erosion of bone leading to malalignment of the joint and disability. The persistent nature of arthritis suggests that not only local but also systemic immune dysfunction, consisting in predominance of the pro-inflammatory response and over production of inflammatory cells and inflammatory substances, such as $CD4^+$ T cells, B cells and inflammatory cytokines. All of which cause long-term destruction to joint tissues. It is generally believed that the infection of a host by unknown exogenous pathogen initiates the course of arthritis through activating T cells, thereby inducing multiple reactions such as the activation of monocytes, macrophages, and directly stimulating the proliferation of synovial and endothelial cells, as well as the production of inflammatory cytokines, protease, and antibody. Further, inflammatory cytokines have been implicated in the arthritis diseases progression. For example, TNF-α is a key player in the proinflammatory cytokine cascade by stimulating the production of prostaglandin E, collagenase as well as other cytokines such as interleukin-1 (IL-1) and interleukin-6 (IL-6). TNF-α and IL-1β also stimulate the secretion of matrix metalloproteinases and exert a direct effect on the multiple tissues inside the joint including chondrocytes, macrophages, synovial fibroblasts, and osteoclasts leading localized joint destruction. On the other hand, IL-6 can further increase inflammatory cells in the joint tissue, stimulate the proliferation of osteoclasts and strengthen the role of IL-1β. Overall, the substantial cross-talk between pro-inflammatory cytokines IL-1δ, TNF-α, IL-6, and IL-17 is essential to induce joint destruction, chondrocyte inhibition, and disturbance for restoration of degenerated tissues in arthritis. Therefore, aside from the traditional immunosuppressive agents and non-steroidal anti-inflammatory drugs, the current clinical majority is to develop biological antagonists specifically aiming at the above-mentioned inflammatory factors or cells, such as TNF-α and IL-6 antagonists, to reduce or prevent joint damage and maintain functionality. However, such therapy is invasive, and the efficacy may subsequently fades. Moreover, at least half of the arthritis patients are not response to the combination of traditional arthritis drugs and biological agents. Therefore, it is important to develop new, convenient, safe and effective therapeutics.

*Plectranthus amboinicus* (Lour.) Spreng, a perennial herb mainly originated from Malaysia, Brazil, China and India, belongs to the Labiatae family, the alias of which are *Agastache rugosa*, *Lysimachia capillipes* Hemsl, Spearmint, Patchouly, Indian peppermint, or *Pogostemon Cablin*. *Plectranthus amboinicus* has leaves that are thick, opposite, widely ovate, toothed on the margin of a little volume with apex rounded or pure sharp. The herb is about 15 to 30 cm high, covered with fine hairs, and carries a strong pungent smell. According to historical records, *Plectranthus amboinicus* is a type of Chinese herbal medicine with the efficacy to prevent colds, strengthen body immunity, and reduce symptoms such as ear swelling, inflammation, and fever. As a traditional Chinese medicine, it is anti-inflammatory, carminative and capable of detoxification and relieving symptoms like fever, tonsillitis, sore throat, pneumonia, chills and heat, headache, nausea of chest and abdomen, vomiting, diarrhea, feeble stomach, spleen cold and others. Fresh juice of *Plectranthus amboinicus* is also effective for abrasions, cuts, burns, insect bites, unknown swelling, boils and sores, ear inflammation, sore throat, swollen poison, bruises and the like. It also has considerable effects on skin problems caused by microorganisms, such as seborrheic dermatitis, eczema, acne, allergies, dry skin, scalp folliculitis, and significant effects on the skin whitening, fatigue elimination, and removal of a variety of skin ringworm.

Taiwan Patent Application No. 092135016 disclosed a method to prepare crude extracts of *Plectranthus amboinicus* (Lour.) Spreng comprising steps of: (a) pressing the plant leaves to obtain juice; (b) adding alcohol to the juice of step (a) to reach a final alcohol concentration at 70-80%, and then placing at a low temperature; (c) adjusting the pH value of the alcohol-containing juice of step (b) to pH5.0~7.0, and then placing at a low temperature; (d) filtering to remove the impurities in the alcohol-containing juice of step (c); (e) distilling and concentrating the resulted pure juice in step (d) to collect the distillate, and adjusting the pH value of such distillate to pH5.0~7.0; and (f) vacuum filtering the distillate in step (e) to obtain dark brown and clear extracts of *Plectranthus amboinicus*.

Taiwan Patent Application No. 093134346 provided a water extract of *Plectranthus amboinicus* leaf having the efficacy to treat cancer and/or tumor which has a molecular weight more than 50 kD.

Taiwan Patent Application No. 086118191 also disclosed a type of water extract of *Pogostemon cablin* or *Agastache rugosa* capable of preventing and treating infection by *Haemophilus influenzae*. The preparation of such extract involves an elution by a reagent composed of 90.5% ethanol, 4.5% methanol and 5.0% isopropanol.

In addition, Taiwan Patent Application No. 096145943, i.e. Taiwan Invention Patent No. I-335225, also provided an extract of *Plectranthus amboinicus* (Lour.) Spreng for treating skin disorders and promoting wound healing, in particular, wound healing in patients with diabetes. The invention as disclosed in this patent is characterized by the use of a combination of the solid-liquid separation (stir separation) and specific processing, which comprises stirring adsorption resin (e.g. DIAION) in the extract of *Plectranthus amboinicus*, and isolating various fractions of such extract by using different solvents in respective separation steps.

Also, Taiwan Patent Application No. 095134243, i.e. Invention Patent No. I320714, disclosed a water extract of *Plectranthus Amboinicus* Benth having the efficacy to treat rheumatoid arthritis. The extract was soaked in an appropriate amount of high-polar solvent, filtered, condensed under reduced pressure by a rotary concentrator, diluted in a solvent, and then separated by in a column. Optionally, four segments of different solvents from high polarity to low polarity (referred to as high-polar solvent, sub high-polar solvent, medium-polar solvent and low-polar solvent) could be used for elution continuously.

BRIEF SUMMARY OF THE INVENTION

The present invention is based on a further development and improvement of the processes for preparing a *Plectranthus amboinicus* extract, which, unexpectedly, exhibited high anti-arthritis activities. Particularly, such extract is prepared by eluting the crude extract of *Plectranthus amboinicus* (Lour.) Spreng by 50%~95% alcoholic solution, or by a normal-phase chromatography.

Accordingly, in one aspect, the present invention provides an extract of *Plectranthus amboinicus* enriching anti-arthritis activity, which is characterized by having an absorption peak of Cirsmaritin at retention time of about 45 min in a HPLC pattern detected at a wavelength of about 320 nm.

In one embodiment of the present invention, the extract of *Plectranthus amboinicus* enriching anti-arthritis activity is characterized by that: said extract was obtained by eluting the crude extract of *Plectranthus amboinicus* using 50%~95% alcoholic solution, preferably using 70%·95% alcoholic solution, and more preferably using about 95% alcoholic solution. In examples of the instant invention, the alcoholic solution is ethanol.

In another embodiment of this invention, the extract of *Plectranthus amboinicus* enriching anti-arthritis activity is obtained by eluting the crude extract of *Plectranthus amboinicus* in a normal phase chromatography using hexane as a first solvent and hexane/ethyl acetate as a second solvent.

In another aspect, the present invention provides a method for preparing an extract of *Plectranthus amboinicus* enriching anti-arthritis activity comprising extracting the plant or dried powder of *Plectranthus amboinicus* in a solvent to obtain a crude extract, and eluting the resulted crude extract by a chromatography using 50%~95% alcoholic solution to isolate an extract enriching anti-arthritis activity.

According to one embodiment of this invention, it is preferable to elute the resulted crude extract using 70%~95% alcoholic solution, and more preferably using about 95% alcoholic solution, to isolate an extract enriching anti-arthritis activity.

In still another aspect, the present invention provides a method for preparing an extract of *Plectranthus amboinicus* enriching anti-arthritis activity comprising extracting the plant or dried powder of *Plectranthus amboinicus* in a solvent to obtain a crude extract, and eluting the resulted crude extract by a normal phase chromatography using hexane as a first solvent and hexane/ethyl acetate as a second solvent to isolate an extract enriching anti-arthritis activity.

In some embodiments of the present invention, the resulted extract enriching anti-arthritis activity can be further eluted by solvents such as ethyl acetate, ethyl acetate/methanol, and/or methanol.

In yet another aspect, the present invention provides a method for preventing or treating arthritis comprising administrating to a subject in need thereof an effective amount of the extract of *Plectranthus amboinicus* enriching anti-arthritis activity as described herein.

In a further aspect, the present invention provides a pharmaceutical composition for preventing or treating arthritis comprising a therapeutically effective amount of an extract of *Plectranthus amboinicus* enriching anti-arthritis activity as described herein, and a pharmaceutically acceptable carrier.

The details of one or more embodiments of the invention are set forth in the description below. Other features or advantages of the present invention will be apparent from the following detailed description of several embodiments, and also from the appended claims.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the preferred embodiments shown.

In the drawings.

DETAILED DESCRIPTION OF THE INVENTION

Unless otherwise defined, all technical and scientific terms used herein have the same meaning as commonly understood by one of ordinary skill in the art to which this invention pertains. In the case of conflict, the present document, including definitions will control.

As used herein, the singular forms "a", "an", and "the" include plural referents unless the context clearly dictates otherwise. Thus, for example, reference to "a sample"

includes a plurality of such samples and equivalents thereof known to those skilled in the art.

As used herein, the term "to prevent" or "preventing" shall generally refer to different degrees of stoppage of action or progress. To prevent is to lessen the degree or to stop something effectually, or both. The term "treatment" or "treating," as used herein, refers to improving conditions.

The term "therapeutically effective amount," as used herein, refers to the amount of components of the composition or the pharmaceutical composition of the invention alone or in combination with other medicaments that could provide therapeutical benefits in treatment.

The present invention provides an extract of *Plectranthus amboinicus* enriching anti-arthritis activity, which is characterized by having an absorption peak of Cirsmaritin at retention time of about 45 min in a HPLC pattern detected at a wavelength of about 320 nm. This can be obtained by eluting the crude extract using 50%~95% alcoholic solution or by a normal phase chromatography. The resulted eluate is different to the known extracts of *Plectranthus amboinicus* in that it is enriched with anti-arthritis activity and thus capable of treating or preventing arthritis.

Figure 3:
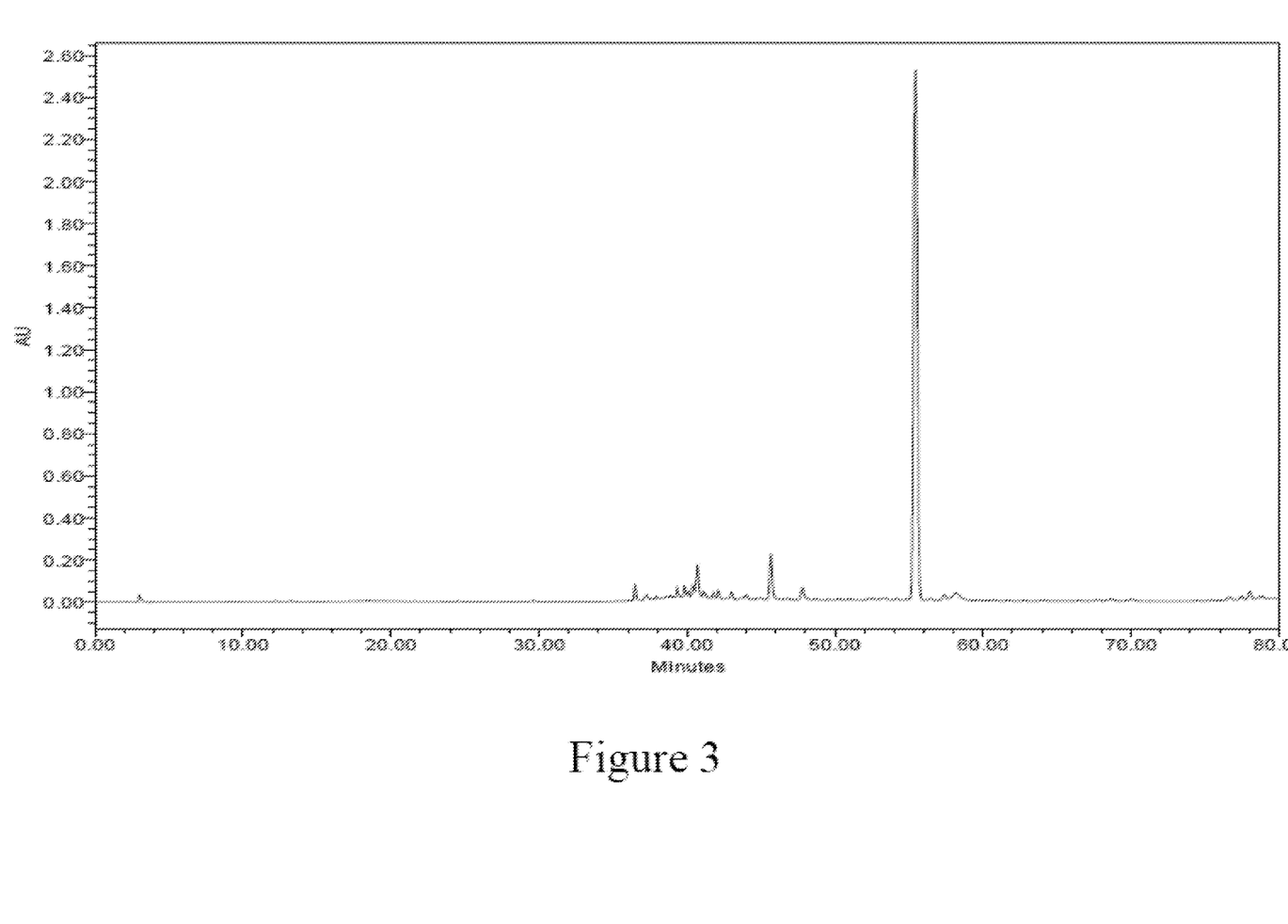
FIG. 3 is a HPLC pattern of ON-025 detected at a wavelength of 200 nm, in which there is an absorption peak at retention time of 45 min, and an absorption peak of Carvacrol at 55 min.
Figure 4:
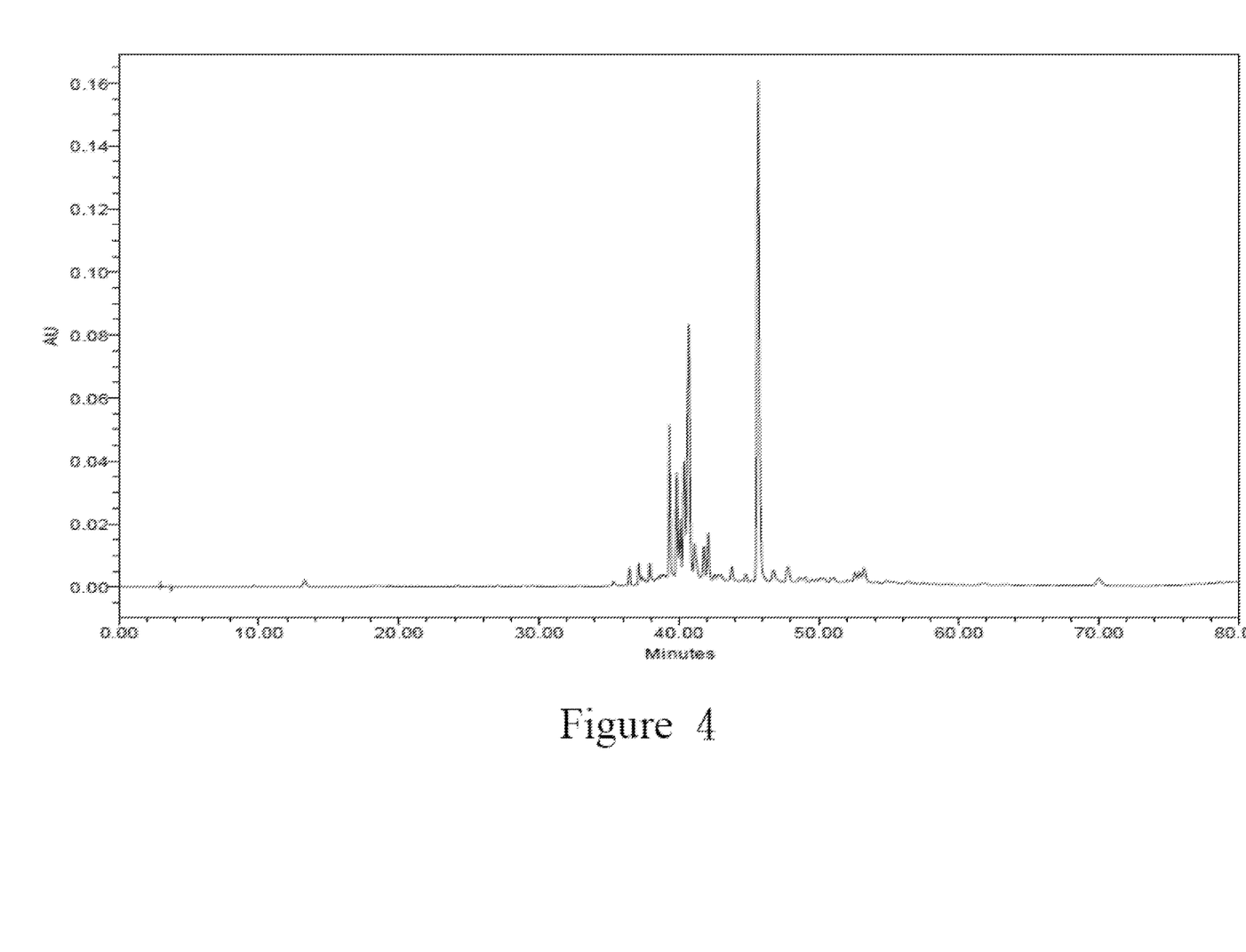
FIG. 4 is a HPLC pattern of ON-025 detected at a wavelength of 320 nm, in which there are eight absorption peaks at retention time of 39-43 min and an absorption peak of Cirsmaritin at 45 min.

According to the present invention, when the extract of *Plectranthus amboinicus* enriching anti-arthritis activity is isolated by eluting the crude extract as described here using 50%~95% alcoholic solution, there is an absorption peak at retention time of about 45 min and an absorption peak of Carvacrol at about 55 min in a HPLC pattern detected at a wavelength of about 200 nm, as shown in FIG. 3; there are also 8 absorption peaks at retention time of 39-43 min and an absorption peak of Cirsmaritin at about 45 min in a HPLC pattern detected at a wavelength of about 320 nm, as shown in FIG. 4.

Figure 5:
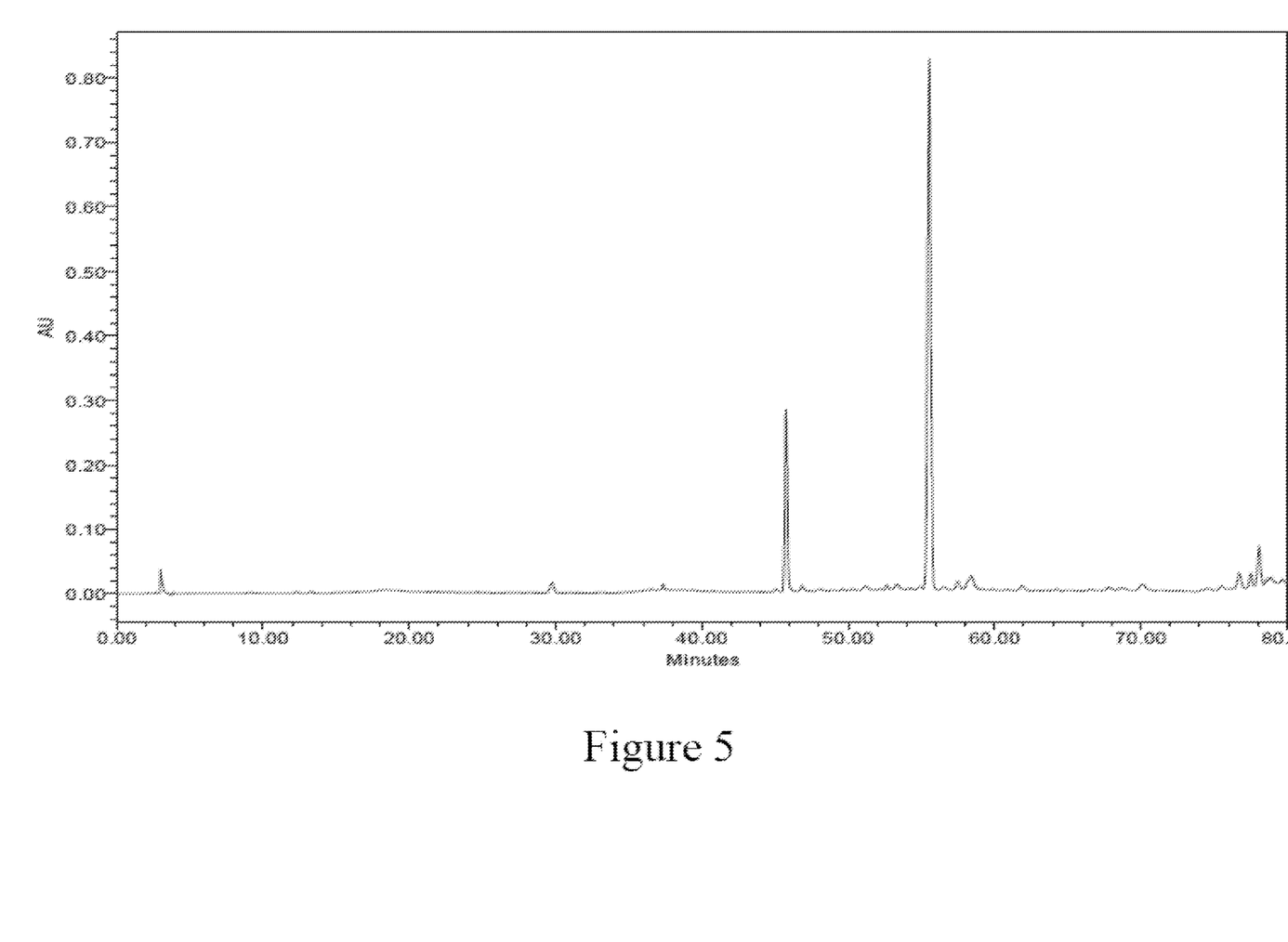
FIG. 5 is a HPLC pattern of ON-066 detected at a wavelength of 200 nm, in which there is an absorption peak of Cirsmaritin at retention time of 45 min and an absorption peak of Carvacrol at 55 min.
Figure 6:
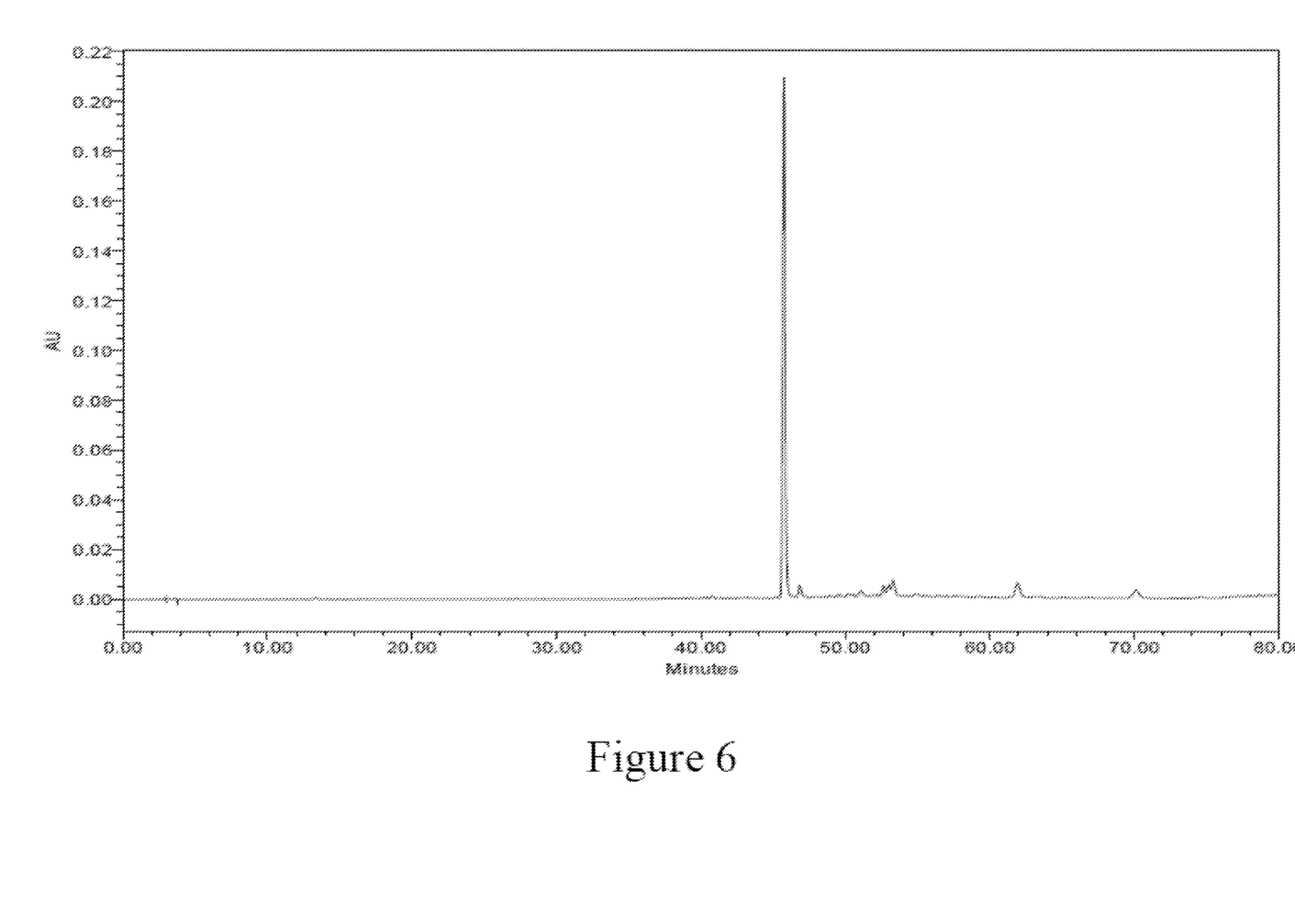
FIG. 6 is a HPLC pattern of ON-066 detected at a wavelength of 320 nm, in which there is an absorption peak of Cirsmaritin at retention time of 45 min and an absorption peak of Salvigenin at 62 min.

According to the present invention, when the extract of *Plectranthus amboinicus* enriching anti-arthritis activity is isolated by eluting the crude extract as described herein using 70%~95% alcoholic solution, there is an absorption peak of Cirsmaritin at retention time of about 45 min and an absorption peak of Carvacrol at about 55 min in a HPLC pattern detected at a wavelength of about 200 nm, as shown in FIG. 5; there are also one absorption peak of Cirsmaritin at retention time of about 45 min and one absorption peak of Salvigenin at about 62 min in a HPLC pattern detected at a wavelength of about 320 nm, as shown in FIG. 6.

Figure 7:
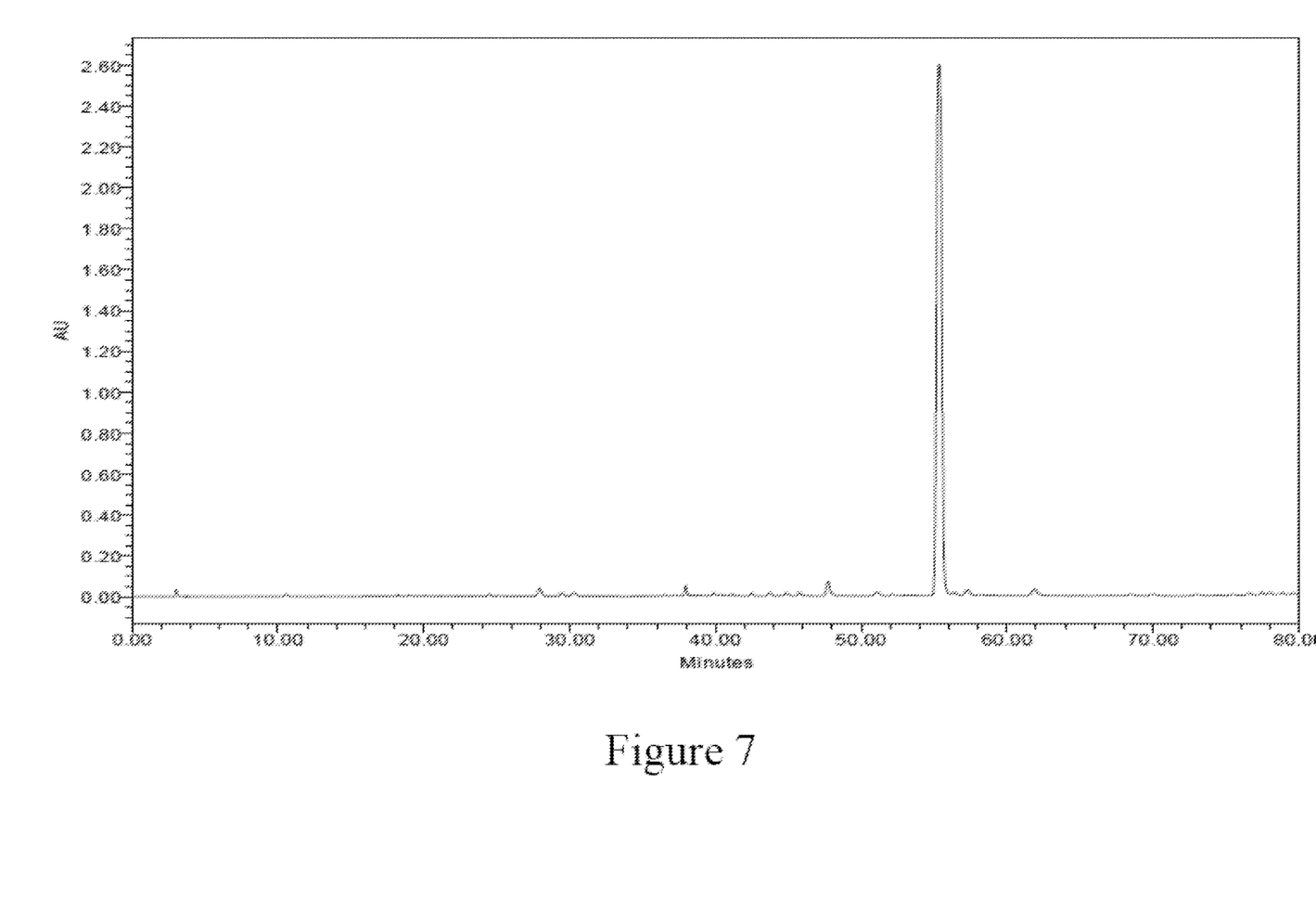
FIG. 7 is a HPLC pattern of ON-080 detected at a wavelength of 200 nm, in which there is an absorption peak of Carvacrol at retention time of 55 min.
Figure 8:
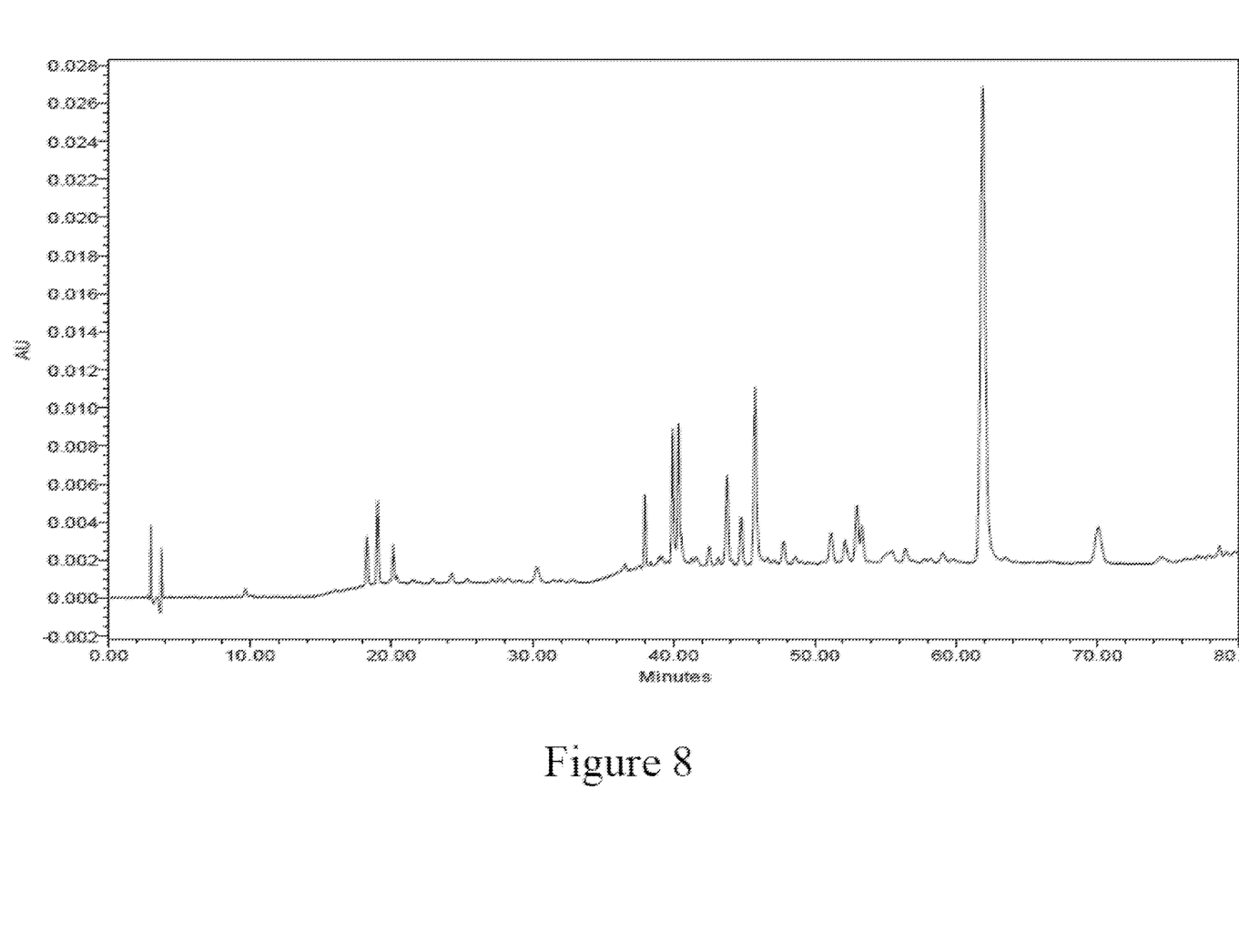
FIG. 8 is a HPLC pattern of ON-080 detected at a wavelength of 320 nm, in which there are three absorption peaks at retention time of 18-21 min, three absorption peaks at 37-41 min, two absorption peaks at 43-45 min, an absorption peak of Cirsmaritin at 45 min, four absorption peaks at 50-54 min, and an absorption peak of Salvigenin at 62 min.

According to the present invention, when the extract of *Plectranthus amboinicus* enriching anti-arthritis activity is isolated by using a normal phase chromatography, there is one absorption peak of Carvacrol at retention time of about 55 min in a HPLC pattern detected at a wavelength of about 200 nm, as shown in FIG. 7; there are also three absorption peaks at retention time of 18-21 min, three absorption peaks at retention time of 37-41 min, two absorption peaks at 43-45 min, one absorption peak of Cirsmaritin at about 45 min, four absorption peaks at 50-54 min, and one absorption peak of Salvigenin at about 62 min in a HPLC pattern detected at a wavelength of about 320 nm, as shown in FIG. 8.

In the present invention, the extract of *Plectranthus amboinicus* enriching anti-arthritis activity can be isolated by a chromatography, which comprises steps of: extracting the plant or dried powder of *Plectranthus amboinicus* in a solvent to obtain a crude extract, and eluting the resulted crude extract by a chromatography using 50%~95% alcoholic solution to isolate an extract enriching anti-arthritis activity.

In one embodiment of this invention, it is preferable to elute the crude extract as described herein by 70%~95% alcoholic solution, or more preferably by about 95% alcoholic solution. According to this invention, the alcoholic solution for elution may be methanol or ethanol. In a preferred embodiment of the instant invention, ethanol is used.

Further provided is a method for preparing an extract of *Plectranthus amboinicus* enriching anti-arthritis activity comprising extracting the plant or dried powder of *Plectranthus amboinicus* in a solvent to obtain a crude extract, and eluting the resulted crude extract by a normal phase chromatography using hexane as a first solvent and hexane/ethyl acetate as a second solvent to isolate an extract enriching anti-arthritis activity. According to one embodiment of this invention, the volume ratio of hexane to ethyl acetate in the solvent "hexane/ethyl acetate" is 1:1.

According to the present invention, *Plectranthus amboinicus* to be extracted can be in any forms as desired, including but not limited to, a fresh or dried plant. It is preferably to extract the plant in the form of powder. The crude extract of the plant can be obtained by any of the known processes, for example, extracting in a solvent, including but not limited to, alcoholic solution. According to one embodiment of the present invention, about 95% ethanol solution is used.

According to one embodiment of the present invention, about 95% ethanol solution can be used to obtain a crude extract, and 70%~95% ethanol solution can be further used in a chromatography to elute and isolate an extract enriching anti-arthritis activity.

In another embodiment of the present invention, about 95% ethanol solution can be used to obtain a crude extract, and hexane can be further used in a normal phase chromatography to elute and isolate an extract enriching anti-arthritis activity.

The extraction process as described herein can be carried out with other appropriate condensation or purification procedures, for example, dry condensation, decompression condensation and freeze-drying.

According to this invention, tests on the rats with arthritis demonstrate that the extract of the instant invention is enriched with anti-arthritis activity. Therefore, the present invention further provides a method for preventing or treating arthritis comprising administrating to a subject in need thereof an effective amount of the extract as described herein.

The present invention also provides a pharmaceutical composition for preventing or treating arthritis comprising a therapeutically effective amount of the extract enriching anti-arthritis activity as described herein and a pharmaceutically acceptable carrier.

An effective amount of the extract enriching anti-arthritis activity in a pharmaceutical composition of this invention for treating arthritis is 0.5~10 g/day.

The most suitable route and dosage for treatment will be easily determined by those skilled in the art. Dosage will depend on the nature and states of the symptoms being treated, ages and general physical conditions of the patient being treated, administration route and any therapies practiced previously.

The term "carrier" or "pharmaceutically acceptable carrier," as used herein, refers to the diluents, excipients, acceptable agents or the like that are well known by those of ordinary skill in the art and can be used in the preparation of pharmaceutical composition.

The composition of the invention can be delivered through any medically acceptable route, such as orally, parentally e.g. intramuscularly, intravenously, subcutaneously, interperitoneally, transdermally, by rectum or inhalation, or vaginal, ocular or nasal routes. The pharmaceutical composition delivered parentally can be in any forms as desired, including but not limited to, solution, suspension, emulsion, and solid injectable composition that is able to dissolve or suspend in a solvent immediately after use. The injectable solution can be prepared by dissolving, suspending, or emulsifying one or more active agents in a diluent. Some examples of the said diluent are distilled water for injection, saline, mineral oils, alcohols, and a combination thereof. The injectable solution can also contain stabilizers, solvents, suspending agents, emulsifying agents, smoothing agents, buffer, preservatives and others. The injectable solution is prepared by sterilization in the final preparation step or by sterile procedures. The pharmaceutical composition of the invention can also be prepared as sterile solid preparations by, for example, freeze-drying, and can be sterilized immediately before use or dissolved in sterile injectable water or other sterile diluents.

The pharmaceutical composition of the present invention can also be delivered orally, the form of which can be solid or liquid. Solid compositions include tablets, pills, capsules, powders, granules and the like. Oral compositions also include gargles and lozenges. Capsules include hard and soft capsules. In such oral solid compositions, one or more active compounds can be used alone or in combination with diluents, chelating agents, disintegrating agents, lubricants, stabilizers, and cosolvents, to form preparations with known methods subsequently. When needed, such preparations can be coated with a coating agent, or two or more coating agents. In another aspect, oral liquid compositions include pharmaceutically acceptable liquid solutions, suspensions, emulsions, syrups, medicated wine, and the like. In such compositions, one or more active compounds can be dissolved, suspended or emulsified in universal diluent (e.g. purified water, ethanol or a combination thereof). Except for such diluent, the above composition can also contain wetting agents, suspending agent, emulsifiers, sweeteners, flavoring agents, spices, preservatives, buffer and the like.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are incorporated herein by reference in their entirety.

EXAMPLES OF PREPARATION

Example 1 Extract Isolated by 50%~95% Ethanol Solution

Preliminary Extraction:

An appropriate amount of dried *Plectranthus amboinicus* was extracted in 95% ethanol solution to obtain a first filtrate. The first filtrate was then filtered to further obtain a residue, which in turn was extracted again in 95% ethanol solution to obtain a second filtrate. Subsequently, the first and the second filtrates were combined and condensed to 1/20 of its original volume under reduced pressure to produce a condensed liquor.

Column Chromatography:

The resulted condensed liquor was separated with a HP-20 column. Briefly, the condensed liquor mixed thoroughly with RO water was applied into the column, followed by passing through the column RO water of four times of the column volume to collect a first eluate. Then, a second eluate was collected by further passing through the column with a solution composed of RO water of four times of the column volume and 95% ethanol in a ratio of 1:1 (v/v). The second eluate was then condensed under reduced pressure and freeze-dried to produce an extract of *Plectranthus amboinicus*, designated as ON-024, i.e. a control sample extracted in 0%~50% ethanol solution.

Subsequently, a third eluate was collected by passing through the column with 95% ethanol solution of four times of the column volume, after which it was condensed under reduced pressure and freeze-dried to produce an extract of *Plectranthus amboinicus*, designated as ON-025, i.e. an extract isolated by 50%~95% ethanol solution.

Further, a fourth eluate was collected by subsequently passing through the column with ethyl acetate, after which it was condensed under reduced pressure and freeze-dried to obtain an extract of *Plectranthus amboinicus* isolated by ethyl acetate.

Example 2 Extract Isolated by 50%~95% Ethanol Solution

Column Chromatography:

The resulted condensed liquor as prepared in Preliminary Extraction of Example 1 was separated with a HP-20 column. Briefly, the condensed liquor mixed thoroughly with RO water was applied into the column, followed by passing two times of the column volume of RO water through the column to collect a first eluate. Then, a second eluate was collected by further passing through the column with a solution composed of two times of the column volume of RO water and 95% ethanol in a ratio of 1:1 (v/v). The second eluate was then condensed under reduced pressure and freeze-dried to produce an extract of *Plectranthus amboinicus*, designated as ON-022.

Subsequently, a third eluate was collected by passing through the column with two times of the column volume of 95% ethanol solution, after which it was condensed under reduced pressure and dried to produce an extract of *Plectranthus amboinicus*, designated as ON-023, i.e. an extract isolated by 50%-95% ethanol solution.

Further, a fourth eluate was collected by subsequently passing through the column with two times of the column volume of ethyl acetate, after which it was condensed under reduced pressure and dried to obtain an extract of *Plectranthus amboinicus* isolated by ethyl acetate.

Example 3 Extract Isolated by 70%-95% Ethanol Solution

The resulted condensed liquor as prepared in Preliminary Extraction of Example 1 was separated with a HP-20 column. Briefly, the condensed liquor mixed thoroughly with RO water was applied into the column, followed by passing through the column with four times of the column volume of RO water to collect a first eluate. Then, a second eluate was collected by further passing through the column with a solution composed of four times of the column volume of RO water and 95% ethanol solution in a ratio of 3:7 (v/v). The second eluate was condensed under reduced pressure and freeze-dried to produce an extract of *Plectranthus amboinicus*, designated as ON-065.

Subsequently, a third eluate was collected by passing through the column with four times of the column volume of 95% ethanol solution, after which it was condensed under reduced pressure and dried to produce an extract of *Plec-

*tranthus amboinicus*, designated as ON-066, i.e. an extract isolated by 70%-95% ethanol solution.

Further, a fourth eluate was collected by subsequently passing through the column with four times of the column volume of ethyl acetate, after which it was condensed under reduced pressure and dried to obtain an extract of *Plectranthus amboinicus* isolated by ethyl acetate.

Example 4 Extract Isolated by Normal Phase Chromatography

Preliminary Extraction:

An appropriate amount of dried *Plectranthus amboinicus* was extracted in 95% ethanol solution to obtain a first filtrate. The first filtrate was then filtered to further obtain a residue, which in turn was extracted again in 95% ethanol solution to obtain a second filtrate. Subsequently, the first and the second filtrates were combined, and condensed under reduced pressure to produce a condensed liquor. Such condensed liquor was then mixed with Silica Gel, followed by condensation under reduced pressure and dried to produce a crude extract attached to the gel ("CE-gel").

Column Chromatography:

Silica Gel in a weight equals to that of the dried *Plectranthus amboinicus* was used to fill the column by use of hexane, after which the filled column was further covered with the CE-gel prepared as described above. Six times of the column volume of hexane was used to elute the column to obtain a first eluate, which was then condensed under reduced pressure and dried to produce an extract of *Plectranthus amboinicus* isolated by hexane, designated as ON-078.

Subsequently, a second eluate was collected by passing through the column with six times of the column volume of hexane/ethyl acetate solution in a ratio of 1:1 (v:v). The resulted second eluate was condensed under reduced pressure and dried to produce an extract of *Plectranthus amboinicus* isolated by hexane/ethyl acetate, designated as ON-079.

Further, a third eluate was collected by subsequently passing through the column with six times of the column volume of ethyl acetate. The resulted third eluate was condensed under reduced pressure and dried to produce an extract of *Plectranthus amboinicus* isolated by ethyl acetate, designated as ON-083.

A fourth eluate was collected by further passing through the column with six times of the column volume of ethyl acetate/methanol solution in a ratio of 1:1 (v/v). The resulted fourth eluate was condensed under reduced pressure and dried to produce an extract of *Plectranthus amboinicus* isolated by ethyl acetate/methanol, designated as ON-084.

A final eluate was collected by subsequently passing through the column with four times of the column volume of methanol. The resulted final eluate was condensed under reduced pressure and dried to produce an extract of *Plectranthus amboinicus* isolated by methanol, designated as ON-085.

Example 5 Extract Isolated by Normal Phase Chromatography

A column chromatography was carried out as described in Example 4 to obtain ON-078.

Subsequently, a second eluate was collected by passing through the column with two times of the column volume of hexane/ethyl acetate solution in a ratio of 1:1 (v:v). The resulted second eluate was condensed under reduced pressure and dried to produce an extract of *Plectranthus amboinicus* isolated by hexane/ethyl acetate, designated as ON-080.

Further, a third eluate was collected by subsequently passing through the column with four times of the column volume of hexane/ethyl acetate solution in a ratio of 1:1 (v:v). The resulted third eluate was condensed under reduced pressure and dried to produce an extract of *Plectranthus amboinicus* isolated by hexane/ethyl acetate, designated as ON-092.

A final eluate was collected by further passing through the column with six times of the column volume of ethyl acetate. The resulted final eluate was condensed under reduced pressure and dried to produce an extract of *Plectranthus amboinicus* isolated by ethyl acetate, designated as ON-083.

Example 6 Extract Isolated by Normal Phase Chromatography

A column chromatography was carried out as described in Example 4 to obtain ON-078.

Subsequently, a second eluate was collected by passing through the column with two times of the column volume of hexane/ethyl acetate solution in a ratio of 1:1 (v:v). The resulted second eluate was condensed under reduced pressure and dried to produce an extract of *Plectranthus amboinicus* isolated by hexane/ethyl acetate, designated as ON-080.

Further, a third eluate was collected by subsequently passing through the column with two times of the column volume of hexane/ethyl acetate solution in a ratio of 1:1 (v:v). The resulted third eluate was condensed under reduced pressure and dried to produce an extract of *Plectranthus amboinicus* isolated by hexane/ethyl acetate, designated as ON-081.

A fourth eluate was collected by subsequently passing through the column with two times of the column volume of hexane/ethyl acetate solution in a ratio of 1:1 (v:v). The resulted fourth eluate was condensed under reduced pressure and dried to produce an extract of *Plectranthus amboinicus* isolated by hexane/ethyl acetate, designated as ON-082.

A fifth eluate was collected by subsequently passing through the column with six times of the column volume of hexane. The resulted fifth eluate was condensed under reduced pressure and dried to produce an extract of *Plectranthus amboinicus* isolated by hexane, designated as ON-083.

A sixth eluate was collected by subsequently passing through the column with six times of the column volume of hexane/methanol solution in a ratio of 1:1 (v:v). The resulted sixth eluate was condensed under reduced pressure and dried to produce an extract of *Plectranthus amboinicus* isolated by hexane/methanol, designated as ON-084.

A final eluate was collected by further passing through the column with four times of the column volume of methanol. The resulted final eluate was condensed under reduced pressure and dried to obtain an extract of *Plectranthus amboinicus* isolated by methanol, designated as ON-085.

Example 7 Extract Isolated by Normal Phase Chromatography

A column chromatography was carried out as described in Example 4 to obtain ON-078.

Subsequently, a second eluate was collected by passing through the column with six times of the column volume of hexane/ethyl acetate solution in a ratio of 9:1 (v:v). A third eluate was collected by passing through the column with six times of the column volume of hexane/ethyl acetate solution in a ratio of 1:1 (v:v). The resulted third eluate was condensed under reduced pressure and dried to produce an extract of *Plectranthus amboinicus* isolated by hexane/ethyl acetate, designated as ON-086.

Example 8 Extract Isolated by Normal Phase Chromatography

A column chromatography was carried out as described in Example 4 to obtain ON-078.

Subsequently, a second eluate was collected by passing through the column with six times of the column volume of hexane/ethyl acetate solution in a ratio of 8:2 (v:v). The resulted second eluate was condensed under reduced pressure and dried to produce an extract of *Plectranthus amboinicus* isolated by hexane/ethyl acetate, designated as ON-087.

A final eluate was collected by subsequently passing through the column with six times of the column volume of hexane/ethyl acetate solution in a ratio of 1:1 (v:v). The resulted final eluate was condensed under reduced pressure and dried to produce an extract of *Plectranthus amboinicus*, designated as ON-088. Example 9 Extract Isolated by Normal Phase Chromatography A Column Chromatography was Carried Out as Described in Example 4 to Obtain ON-078

Subsequently, a second eluate was collected by passing through the column with six times of the column volume of hexane/ethyl acetate solution in a ratio of 7:3 (v:v). The resulted second eluate was condensed under reduced pressure and dried to produce an extract of *Plectranthus amboinicus* isolated by hexane/ethyl acetate, designated as ON-089.

A final eluate was collected by further passing through the column with six times of the column volume of hexane/ethyl acetate solution in a ratio of 1:1 (v:v). The resulted final eluate was condensed under reduced pressure and dried to produce an extract of *Plectranthus amboinicus*, designated as ON-090.

Example 10 Extract Isolated by Normal Phase Chromatography

A column chromatography was carried out as described in Example 4 to obtain ON-078.

Subsequently, a second eluate was collected by passing through the column with six times of the column volume of hexane/ethyl acetate solution in a ratio of 6:4 (v:v). The resulted second eluate was condensed under reduced pressure and dried to produce an extract of *Plectranthus amboinicus* isolated by hexane/ethyl acetate, designated as ON-091.

Figure 1:
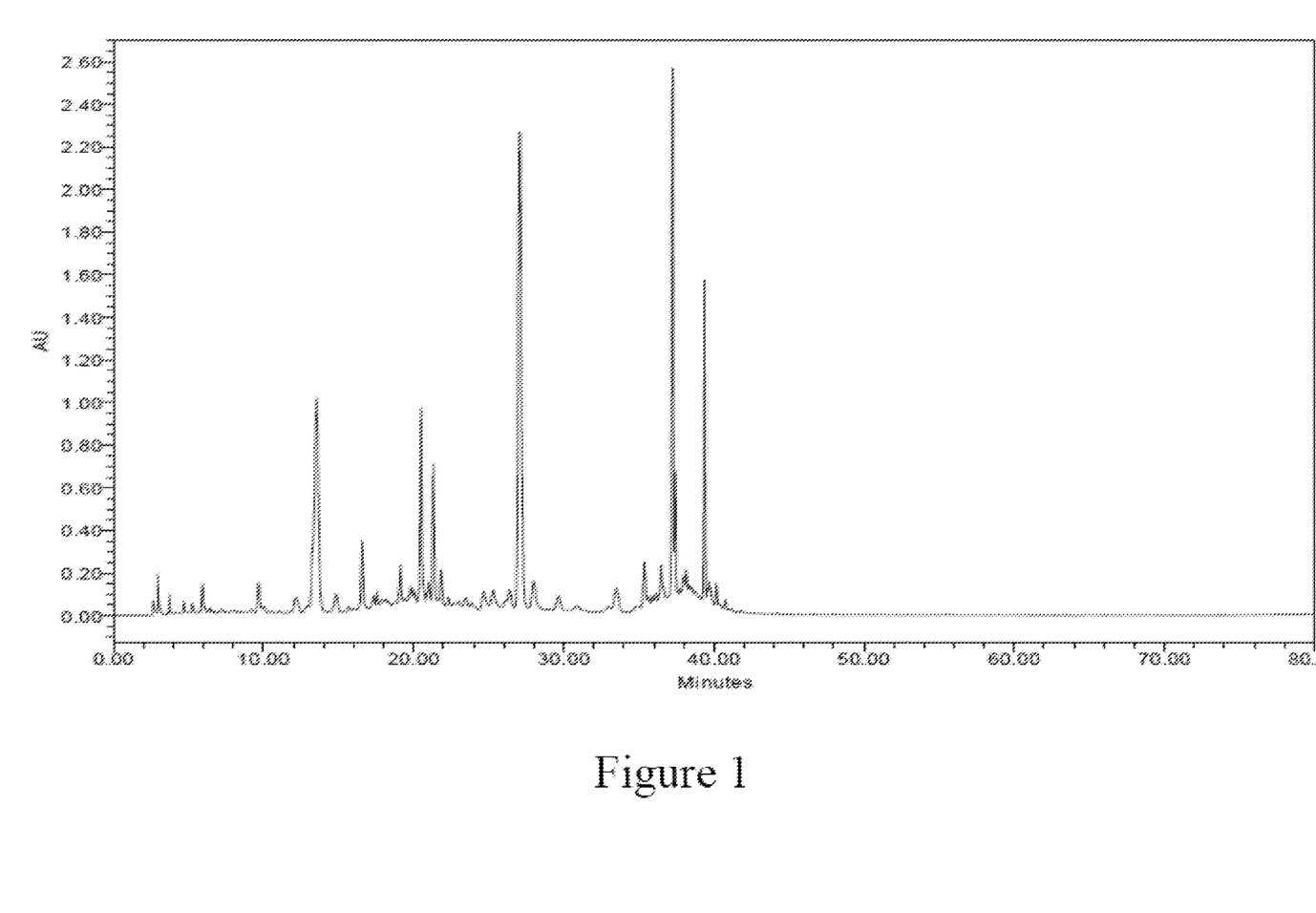
FIG. 1 is a HPLC pattern of ON-024 detected at a wavelength of 200 nm, in which there are six absorption peaks at retention times of 13, 20, 21, 27, 37 and 39 min.
Figure 2:
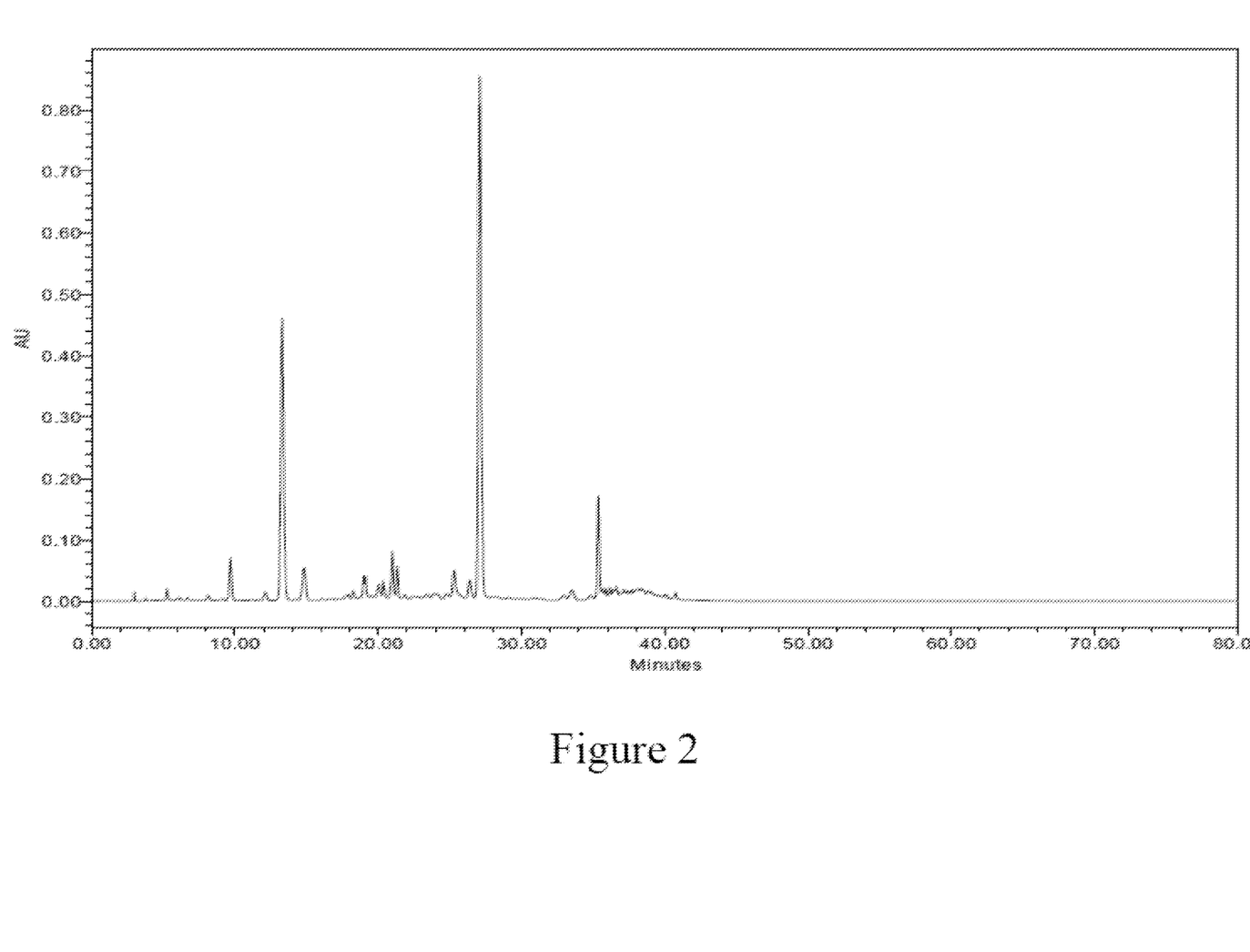
FIG. 2 is a HPLC pattern of ON-024 detected at a wavelength of 320 nm, in which there is an absorption peak of Caffeic acid at retention time of 13 min, an absorption peak of Rosmarinic acid at 27 min, and an absorption peak at 35 min.

We further analyze the extracts of ON-024 (an extract isolated by 0%~50% ethanol solution), ON-025 (an extract isolated by 50%~95% ethanol solution), ON-066 (an extract isolated by a 70%-95% ethanol solution), and ON-080 (an extract isolated by a normal phase chromatography) by high performance liquid chromatography (HPLC) detecting at a wavelength of 200 nm and 320 nm. As a result, the HPLC pattern of ON-024 was found to be different to those of ON-025 (an extract isolated by 50%-95% ethanol solution), ON-066 (an extract isolated by 70%~95% ethanol solution) and ON-080 (an extract isolated by a normal phase chromatography):

(1) The HPLC pattern of ON-024 detected at a wavelength of 200 nm showed six absorption peaks at retention times of 13, 20, 21, 27, 37 and 39 min (FIG. 1); and that detected at a wavelength of 320 nm showed an absorption peak of Caffeic acid at retention time of 13 min, an absorption peak of Rosmarinic acid at 27 min, and an absorption peak at 35 min (FIG. 2).

(2) The HPLC pattern of ON-025 detected at a wavelength of 200 nm showed an absorption peak at retention time of 45 min, and an absorption peak of Carvacrol at 55 min (FIG. 3); and that detected at a wavelength of 320 nm showed eight absorption peaks at retention time of 39-43 min and an absorption peak of Cirsmaritin at 45 min (FIG. 4).

(3) The HPLC pattern of ON-066 detected at a wavelength of 200 nm showed an absorption peak of Cirsmaritin at retention time of 45 min and an absorption peak of Carvacrol at 55 min (FIG. 5); and that detected at a wavelength of 320 nm showed an absorption peak of Cirsmaritin at retention time of 45 min and an absorption peak of Salvigenin at 62 min (FIG. 6).

(4) The HPLC pattern of ON-080 detected at a wavelength of 200 nm showed an absorption peak of Carvacrol at retention time of 55 min (FIG. 7); and that detected at a wavelength of 320 nm showed three absorption peaks at retention time of 18-21 min, three absorption peaks at 37-41 min, two absorption peaks at 43-45 min, an absorption peak of Cirsmaritin at 45 min, four absorption peaks at 50-54 min, and an absorption peak of Salvigenin at 62 min (FIG. 8).

Examples of Efficacy

Example 1 Animal Models with Complete Freund's Adjuvant-Induced Arthritis

Groups of 6 female Lewis rats weighing 170±10 g were used. Complete Freund's Adjuvant (CFA), a well-ground suspension of killed *Mycobacterium butyricum* (0.3 mg in 0.1 ml of light mineral oil), was injected in a single dose into the sub-plantar region of the right hind paw (denoted Day 1). One hour before the injection of CFA, vehicle (1% carboxymethylcellulose, 10 mL/kg) or the test compounds at 500 mg/kg were administered to the animals by oral gavage (PO). The administrations were carried out twice daily for 5 consecutive days. The volumes of the left hind paws were measured by plethysmometer on Day 0 (before CFA treatment), Day 14, Day 18, and Day 21. The net swelling of each treatment group was then compared to vehicle-treated group and expressed as percentage of inhibition. An inhibition of 30% or more in paw volume relative to the vehicle-treated control is considered significant anti-arthritis activity. The extract administered to each group and the corresponding results are also shown in Table 1 below:

TABLE 1

Inhibition Activity Relative to the Control Group

| | | Inhibition Relative to Vehicle Control (%) | | |
|---|---|---|---|---|
| Treatment | Dose | Day 14 | Day 18 | Day 21 |
| ON-022 | 500 mg/kg, bid × 5, PO | 12 | 21 | 16 |
| ON-023 | 500 mg/kg, bid × 5, PO | 44* | 55* | 53* |

TABLE 1-continued

Inhibition Activity Relative to the Control Group

| | | Inhibition Relative to Vehicle Control (%) | | |
|---|---|---|---|---|
| Treatment | Dose | Day 14 | Day 18 | Day 21 |
| ON-024 | 500 mg/kg, bid × 5, PO | 24 | 15 | 27 |
| ON-025 | 500 mg/kg, bid × 5, PO | 56* | 53* | 46* |
| ON-026 | 500 mg/kg, bid × 5, PO | 29 | 22 | 3 |
| ON-065 | 500 mg/kg, bid × 5, PO | 24 | 14 | 23 |
| ON-066 | 500 mg/kg, bid × 5, PO | 45* | 42* | 48* |
| ON-080 | 500 mg/kg, bid × 5, PO | 36* | 42* | 42* |

"*" indicates significant anti-arthritis activity.

As shown in Table 1, extracts of the present invention are enriched with anti-arthritis activity, in particular, the extracts of ON-023, ON-025, ON-066, and ON-080.

Example 2 Anti-Inflammation Activity

Experiments (A) Cell Culture

The peripheral blood mononuclear cells (PBMCs) from the blood of healthy adult donors were diluted and isolated by Ficoll-Paque (FP) gradient centrifugation (Amersham Biosciences) at 600 g for 30 min at room temperature. The isolated PBMCs were washed by phosphate buffered saline, re-suspended in 10% heat inactivated fetal bovine serum (FBS), and seeded in 96-well culture plate with a density of 2.0×10 cells per well for assessing the anti-arthritis activity of the extracts as described herein.

(B) Inhibition of PHA-Induced PBMC Proliferation

PHA-induced PBMC proliferation was used as a technical platform for the assessment of anti-inflammation efficacy of various extracts of the present invention. Human PBMCs were co-cultured with PHA at a final concentration of 5 µg/mL and various extracts of *Plectranthus amboinicus* at a final concentration of 0~90 µg/mL for 3 days. PBMCs treated by dexamethasone (DEX) before stimulation by PHA (5 µg/mL) were also included in the experiment as positive control samples. After cells were incubated for 3 days at 37° C. with humid air containing 5% $CO_2$, MTT (methyl thiazolyl tetrazolium, MTT) assays were carried out to evaluate the proliferation rate of PBMCs. PBMCs without PHA treatment were used as negative control samples. The absorbance of each well was detected by a photoelectric colorimeter at the wavelength of 540 nm. The color intensity was proportional with the degree of cell proliferation; and therefore can be used to calculate the inhibition activity of each extract. Three independent experiments were performed, and the data determined by MTT assays were further expressed as $IC_{50}$.

As shown in Tables 2 and 3, the extracts of *Plectranthus amboinicus* provided by the instant invention were all found to be capable of inhibiting the proliferation of lymphocytes induced by PHA in a dose dependent manner. The cytotoxicity of the extracts to cell (without PHA treatment) was also determined by MTT assays. As a result, ON-023 (40 µg/mL) showed complete inhibition activity to PHA-induced lymphocyte proliferation without cytotoxicity; on the contrary, ON-022 (40 µg/mL) showed only partial inhibition activity (~50%) to PHA-induced lymphocyte proliferation.

TABLE 2

Inhibition of various extracts to PHA-induced PMBC proliferation (data were determined by MTT assays)

| | Concentration of sample (ug/mL) | | | | | |
|---|---|---|---|---|---|---|
| Sample | 1.25 | 2.5 | 5 | 10 | 20 | 40 |
| Example 2__ON-022 | 0.589 | 0.536 | 0.513 | 0.520 | 0.511 | 0.405 |
| Example 2__ON-023 | 0.649 | 0.637 | 0.559 | 0.533 | 0.426 | 0.154 |
| Example 1__ON-024 | 0.651 | 0.591 | 0.603 | 0.576 | 0.504 | 0.231 |
| Example 1__ON-025 | 0.740 | 0.749 | 0.744 | 0.703 | 0.611 | 0.374 |
| Example 3__ON-065 | 0.570 | 0.534 | 0.518 | 0.485 | 0.383 | 0.151 |
| Example 3__ON-065 | 0.580 | 0.522 | 0.457 | 0.357 | 0.301 | 0.190 |
| Negative control group (without PHA) | 0.245 | | | | | |
| PHA | 0.634 | | | | | |
| DEX 0.1 uM | 0.242 | | | | | |

TABLE 3

Inhibition of various extracts to PHA-induced PMBC proliferation (data were determined by MTT assays and expressed as $IC_{50}$)

| Sample | $IC_{50}$ (ug/ml) |
|---|---|
| ON-022 | 36.1 |
| ON-023 | 11.6 |
| ON-024 | 22.2 |
| ON-025 | 21.5 |
| ON-065 | 15.5 |
| ON-066 | 6.1 |
| ON-078 | >50 |
| ON-079 | <5.6 |
| ON-080 | 11.6 |
| ON-081 | 40.7 |
| ON-082 | 8.5 |
| ON-083 | >55.5 |
| ON-084 | >55.5 |
| ON-085 | >55.5 |
| ON-086 | 32 |
| ON-087 | 7.1 |
| ON-088 | 39.3 |
| ON-089 | 14.2 |
| ON-090 | 27.7 |
| ON-091 | 12.3 |

(C) Production and Measurement of PHA-Induced Cytokines

On Day 3, cell supernatant was collected, divided, and stored at −20° C. until analysis. The amounts of TNF-α, interleukin IL-6, IFN-γ, and IL-5 in the supernatant were measured using Quantikine ELISA kits (R & D Systems, Minneapolis, Minn.) following the manufacturer's instruction.

The levels of cytokines in the culture medium, either released spontaneously or induced by PHA, are shown in Table 4. The effect of each extract on PHA-induced cytokine production from PBMCs is shown in Tables 5-8. These results demonstrated the anti-inflammation effects of the extracts of the present invention.

TABLE 4

PHA-induced release of TNF-α, IL-6, IFN-γ & IL-5 (pg/mL) from PBMCs

| | Concentration of Cytokines (pg/mL) | | | |
|---|---|---|---|---|
| | TNF-α | IL-6 | IFN-γ | IL-5 |
| Control Group (without PHA) | 271.6 | 157 | 25.0 | 37.0 |
| PHA | 4031.3 | 703.0 | 176.8 | 161.9 |
| PHA + 0.1uM DEX | 272.5 | 157 | 25 | 37 |

TABLE 5

Inhibition of various extracts to PHA-induced TNF-α release from PBMCs

| | Concentration of Sample (ug/mL) | | | |
|---|---|---|---|---|
| Sample | 5 | 10 | 20 | 40 |
| Example 2_ON-022 | 5257.1 | 4138.9 | 4129.4 | 2884.3 |
| Example 2_ON-023 | 3807.3 | 2744.9 | 881.6 | 126.0 |
| Example 1_ON-024 | 1784.0 | 1549.2 | 1048.8 | 126.0 |
| Example 1_ON-025 | 3323.6 | 3053.3 | 2872.4 | 683.9 |
| Example 3_ON-065 | 1517.4 | 937.8 | 251.5 | 126.0 |
| Example 3_ON-065 | 6090.6 | 6782.1 | 4445.6 | 742.4 |

TABLE 6

Inhibition of various extracts to PHA-induced IL-6 release from PBMCs

| | Concentration of Sample (ug/mL) | | | |
|---|---|---|---|---|
| Sample | 5 | 10 | 20 | 40 |
| Example 2_ON-022 | 849.2 | 567.2 | 511.8 | 157.0 |
| Example 2_ON-023 | 804.8 | 1131.5 | 788.6 | 157.0 |
| Example 1_ON-024 | 466.6 | 498.4 | 292.6 | 157.0 |
| Example 1_ON-025 | 1073.1 | 1205.5 | 1198.0 | 363.0 |
| Example 3_ON-065 | 421.7 | 330.5 | 390.1 | 157.0 |
| Example 3_ON-065 | 4407.3 | 4693.9 | 2367.7 | 196.6 |

TABLE 7

Inhibition of various extracts to PHA-induced IFN-γ release from PBMCs

| | Concentration of sample (ug/mL) | | | |
|---|---|---|---|---|
| Sample | 5 | 10 | 20 | 40 |
| Example 2_ON-022 | 169.3 | 164.2 | 259.9 | 89.6 |
| Example 2_ON-023 | 42.5 | 25.0 | 25.0 | 25.0 |
| Example 1_ON-024 | 43.8 | 83.4 | 25.0 | 25.0 |
| Example 1_ON-025 | 143.3 | 166.1 | 216.9 | 25.0 |
| Example 3_ON-065 | 79.0 | 68.7 | 25.0 | 25.0 |
| Example 3_ON-065 | 667.2 | 528.2 | 379.8 | 25.0 |

TABLE 8

Inhibition of various extracts to PHA-induced IL-5 release of PBMCs

| | Concentration of sample (ug/mL) | | | |
|---|---|---|---|---|
| Sample | 5 | 10 | 20 | 40 |
| Example 2_ON-022 | 155.3 | 156.0 | 127.6 | 78.9 |
| Example 2_ON-023 | 168.5 | 156.7 | 115.8 | 37.0 |
| Example 1_ON-024 | 147.7 | 140.8 | 117.9 | 37.0 |
| Example 1_ON-025 | 183.1 | 184.5 | 228.4 | 109.5 |
| Example 3_ON-065 | 140.8 | 112.3 | 74.0 | 37.0 |
| Example 3_ON-065 | 54.4 | 163.7 | 185.2 | 58.6 |

What is claimed is:

1. A method for preparing an extract of *Plectranthus amboinicus* (Lout.) Spreng enriching anti-arthritis activity comprising: extracting dried *Plectranthus amboinicus* (Lour.) Spreng in a 95% ethanol solution to obtain a crude extract, and eluting the resulted crude extract by a normal phase chromatography via a silica gel column using solvents consisting of: hexane as a first solvent and hexane/ethyl acetate in a ratio of 1:1 (v:v) as a second solvent to isolate an extract enriching anti-arthritis activity by the second solvent;

wherein the obtained extract of *Plectranthus amboinicus* (Lour.) Spreng is characterized by having 59.19 mg/g or more Carvacrol.

2. A pharmaceutical composition for treating arthritis comprising a therapeutically effective amount of the extract as prepared by the method of claim 1, and a pharmaceutically acceptable carrier;

wherein the extract of *Plectranthus amboinicus* (Lour.) Spreng is characterized by having 59.19 mg/g or more Carvacrol.

* * * * *